(12) United States Patent
Berry et al.

(10) Patent No.: US 6,934,642 B2
(45) Date of Patent: Aug. 23, 2005

(54) METHOD FOR DETERMINING SUPERFICIAL RESIDUAL STRESS AS APPLIED TO MACHINED, MECHANICALLY OR THERMALLY PROCESSED SURFACES

(75) Inventors: John T. Berry, Columbus, MS (US); John E. Wyatt, Mississippi State, MS (US)

(73) Assignee: Mississippi State University, Mississippi State, MS (US)

( * ) Notice: Subject to any disclaimer, the term of this patent is extended or adjusted under 35 U.S.C. 154(b) by 0 days.

(21) Appl. No.: 10/825,181

(22) Filed: Apr. 16, 2004

(65) Prior Publication Data

US 2004/0267462 A1 Dec. 30, 2004

Related U.S. Application Data

(60) Provisional application No. 60/463,160, filed on Apr. 16, 2003.

(51) Int. Cl.[7] ............................................. G06F 19/00
(52) U.S. Cl. ............................ 702/42; 702/43; 702/105
(58) Field of Search .............................. 702/33, 34, 35, 702/36, 42, 43, 105, 158, 163; 73/78, 81, 760, 761

(56) References Cited

U.S. PATENT DOCUMENTS 4,964,305 A * 10/1990 Raulins ....................... 73/761
6,643,488 B1 * 11/2003 Yoshida ...................... 399/308
6,721,667 B2 * 4/2004 Banes et al. ................... 702/41

OTHER PUBLICATIONS

Proffen, et al., Interactive Guide to Diffraction, http://www.uni-wuerzburg.de/mineralogie/crystal/teaching/teaching.html (2003). 8 pages.

Simes, et al., "A Note on the Influence of Residual Stress on Measured Hardness, Research Note", Journal of Strain Analysis,19(2):135–137 (1984).

Tissue B.M., Chemistry Hypermedia Project, http://www.chem.vt.edu/chem–ed/diffraction/neutron.html (2000). 4 pages.

* cited by examiner

*Primary Examiner*—Bryan Bui
(74) *Attorney, Agent, or Firm*—DLA Piper Rudnick Gray Cary US LLP

(57) ABSTRACT

A novel economical method for determining the residual stress levels in machined, mechanically or thermally processed components and for determining whether the stress is tensile or compressive. Also provided is a system including components for accomplishing the method of the present invention. Also provided is a method of modeling of a component residual stress from production of raw billet through to a finished component.

63 Claims, 3 Drawing Sheets

METHOD FOR DETERMINING SUPERFICIAL RESIDUAL STRESS AS APPLIED TO MACHINED, MECHANICALLY OR THERMALLY PROCESSED SURFACES

This application claims priority from U.S. Provisional Application Ser. No. 60/463,160 filed Apr. 16, 2003. The entirety of that provisional application is incorporated herein by reference.

BACKGROUND OF THE INVENTION

1. Field of the Invention

This invention relates to novel, economical methods for determining the residual stress levels in machined, mechanically or thermally processed components and whether the stress is tensile or compressive. This invention also relates to a method of modeling of a component residual stress from production of raw billet through to a finished component.

2. Background of the Technology

Machining is the principal manufacturing process in the world with some 10–15% of the value of all goods being attributed either directly or indirectly to machining [Merchant, 1999]. However, with today's economic climate demanding products to be manufactured at increasingly reduced cost, machining cycle times have dramatically dropped. The use of high speed machining (HSM) techniques allows for high material removal rates, which in turn reduces machining cycle times [Dewes et al., 1995; Wyatt, 2002, Dewes et al., 1996; Smith et al., 1998]. Unfortunately, the capital cost of the equipment employed in HSM is high, which leaves machine shops that cannot make this type of investment in a precarious position with regard to the market place that they serve.

Conventional CNC machine shops are looking at increasing their machining parameters such as cutting speeds and feed rates etc. to improve productivity. However, these increases in speeds and feeds can lead to the machined surface, although visually acceptable, becoming abused. This abuse of the finished surface can lead to the component suffering from premature failure as a result of residual stresses that have been induced by the more abusive machining regime that the current market place has dictated.

Residual stress in a machined component is critical in determining both the wear and the fatigue characteristics of that component [Liu et al., 1984; Arndt, 1971]. It is not just the levels of stress that are critical but whether the stress is tensile or compressive. A machined surface that has tensile residual stress induced by the machining process would be prone to fatigue cracking whereas a machined surface with compressive residual stress would be resistant to fatigue cracking [Kalpakjian, 2001].

The experimental study of residual stresses associated with machined surfaces goes back at least fifty years [Henricksen, 1951]. Much of the early work was concerned with turning operations in an attempt to simplify the subsequent analysis of the mechanical state obtained. Extensive progress has since been made using a finite element method based approach to predicting residual stress distributions present after machining. Investigators have considered the highly important effects of sequential cutting action, as well as un-cut chip thickness in their simulations [Liu et al., 2000;Guo et al., 2000]. Those investigators have presented both residual stress profiles from the machined surface inwards, as well as the stress strain history of surface elements in their studies. Dominating are the effects of un-cut chip thickness in controlling the nature of the residual stress in the direction of the cut (tension versus compression).

In several of the experiments mentioned above, the investigators have assumed an initial state of zero stress and strain in the elements concerned. However, it is recognized that for heavy sections where there exist significantly differing cooling histories after heat treatment, for example thick aluminum alloy plate, the initial state of residual stress must be taken into account in subsequent modeling. Pechiney, has used such information in their simulations on the machining of billet intended for aerospace applications [Heymes et al., 1997]. Consequently, both material as well as final mechanical states must be taken into account if effects of subsequent behavior in monotonic or repeated loading are to be predicted.

Recent work on wrought aluminum alloys by SAAB, studied the effect of high speed machining on the fatigue strength of an aluminum workpiece [Ansell 1999]. The results were compared with those for samples that were prepared by conventional machining. The aluminum alloy was 7010-T7451, and panels were produced using different methods of machining. Fatigue test data showed that first a decrease in fatigue resistance was observed when the cutting speed increased above the conventional speed level, 100 m/min, but then an increase occurred when the cutting speed was raised towards 3,000 m/min. The minimum resistance appeared to be in the speed range of 200 to 500 m/min. The fatigue life of the specimens was also dependant upon the cutting mode employed. Climb milling was shown to give the largest reduction in fatigue resistance, while face cut milling seemed to develop a less serious reduction. Up-cut milling also gave a considerable reduction but less than that of climb milling. (See FIG. 1).

In reviewing the SAAB investigation [Blom et al., 2001], the Swedish Defense Research Agency presented an S–N curve indicating a serious reduction in fatigue life for various maximum stress levels. (See FIG. 2). Other researchers have suggested that high speed machining can be beneficial. For example, work at Sikorsky Aircraft supported by residual stress measurements at United Technologies Research Center [Fitzsimmons et al., 2000] suggests that near surface residual stresses in ground surfaces of a wrought titanium alloy can become tensional, whereas with the high speed machined condition chosen (not specified) the sub-surface residual stresses are predominantly compressive.

From an analysis of the work that has previously been undertaken there is still much that is not understood about how residual stresses are formed in high speed machining [Marchal, 2003;Peyronel, 2002]. It is felt that there may be windows of opportunity that high speed machining can exploit to give excellent fatigue life but that these areas have not yet been mapped, as shown in FIG. 1.

The current state of the art to measure residual stress is through the use of X-ray diffraction or neutron diffraction to measure residual stresses at a sub-microscopic level. Such methods measure how much the atomic spacing in the lattice structure of the material has changed and then calculates the residual stress from these measurements. However, these methods are both expensive and technically complicated to operate. There remains therefore a need for an accurate, easy to use, and economical method to measure residual stress.

SUMMARY OF THE INVENTION

The present invention provides a method of determining the residual stress of a material that includes: marking the material with two or more gage marks, measuring the first distance between the gage marks, stress relieving the material, measuring the second distance between the gage marks, and calculating the difference between the first distance and the second distance and thereby determining the amount of elastic residual strain in the material.

Also provided is a method of determining the residual stress of a material that includes: marking the material with one or more sets of gage marks or lines, measuring the first distance between the gage marks or lines, stress relieving the material, measuring a second distance between the gage marks or lines, and calculating the difference between the first distance and the second distance and thereby determining the amount of elastic residual strain in the material.

Also provided is a system that can be used to determine the residual stress of a material, the system including: a marking device for marking the material with one or more sets of gage marks or lines, a measuring device for measuring a first distance between the gage marks or lines, a device for stress releasing the material, a second measuring device for measuring a second distance between the gage markers or lines, a calculating device for calculating the difference between the first distance and the second distance and thereby determining the amount of elastic residual strain in the material.

Also provided is a system that can be used to determine the residual stress of a material, the system including: a means for marking the material with one or more sets of gage marks or lines, a means for measuring the first distance between the gage marks or lines, a means for stress relieving the material, a means for measuring a second distance between the gage marks or lines, and a means for calculating the difference between the first distance and the second distance and thereby determining the amount of elastic residual strain in the material.

Also provided is a method of determining residual stress levels and whether they are tensile or compressive in nature.

Also provided is a method of modeling of a component residual stress from production of raw billet through to finished machined component.

DETAILED DESCRIPTION OF THE INVENTION

Figure 1:
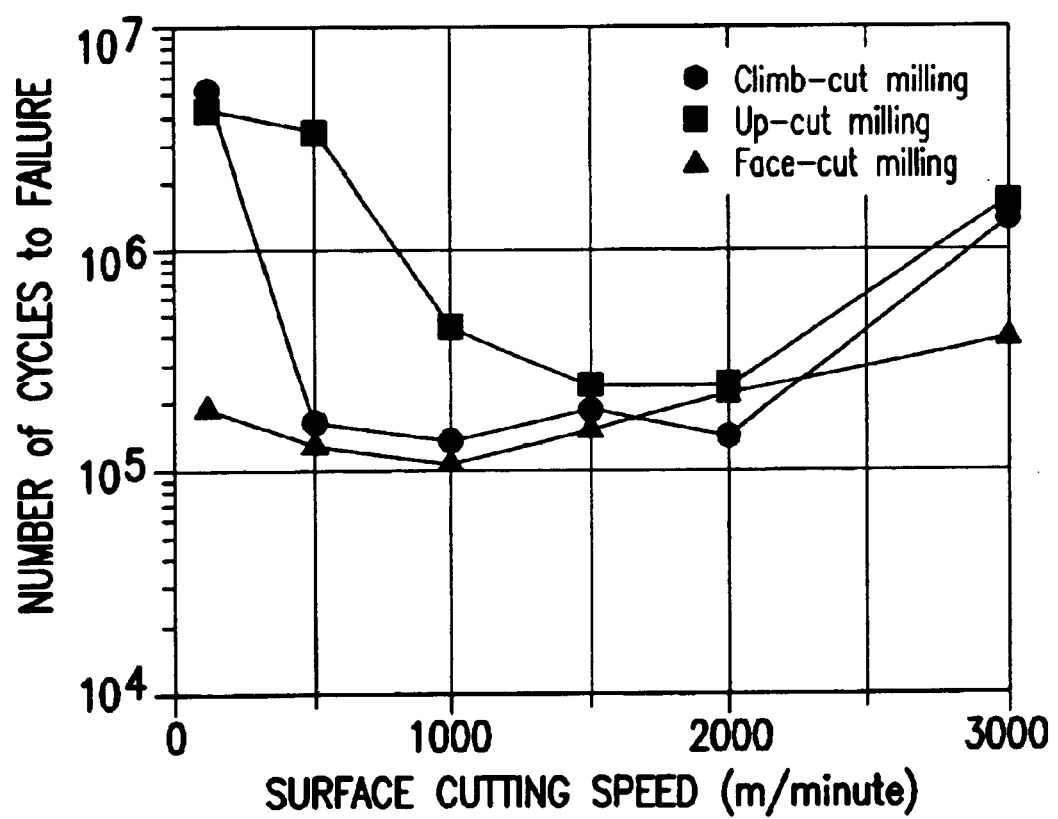
FIG. 1 is a graphic display indicating Ansell's data on the effect of high speed machining on the fatigue strength of the material being machined. [Ansell 1999].
Figure 2:
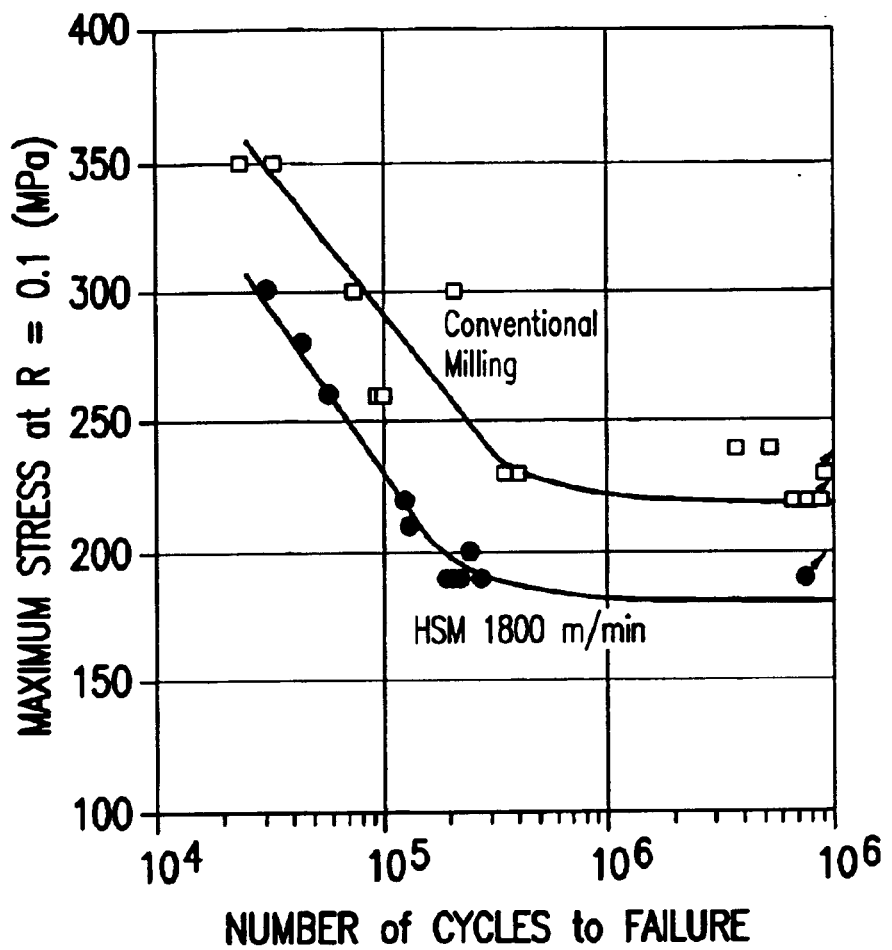
FIG. 2 is a graphic display indicating Blom's data showing a serious reduction in fatigue life or various maximum stress levels. [Blom et al., 2001].
Figure 3:
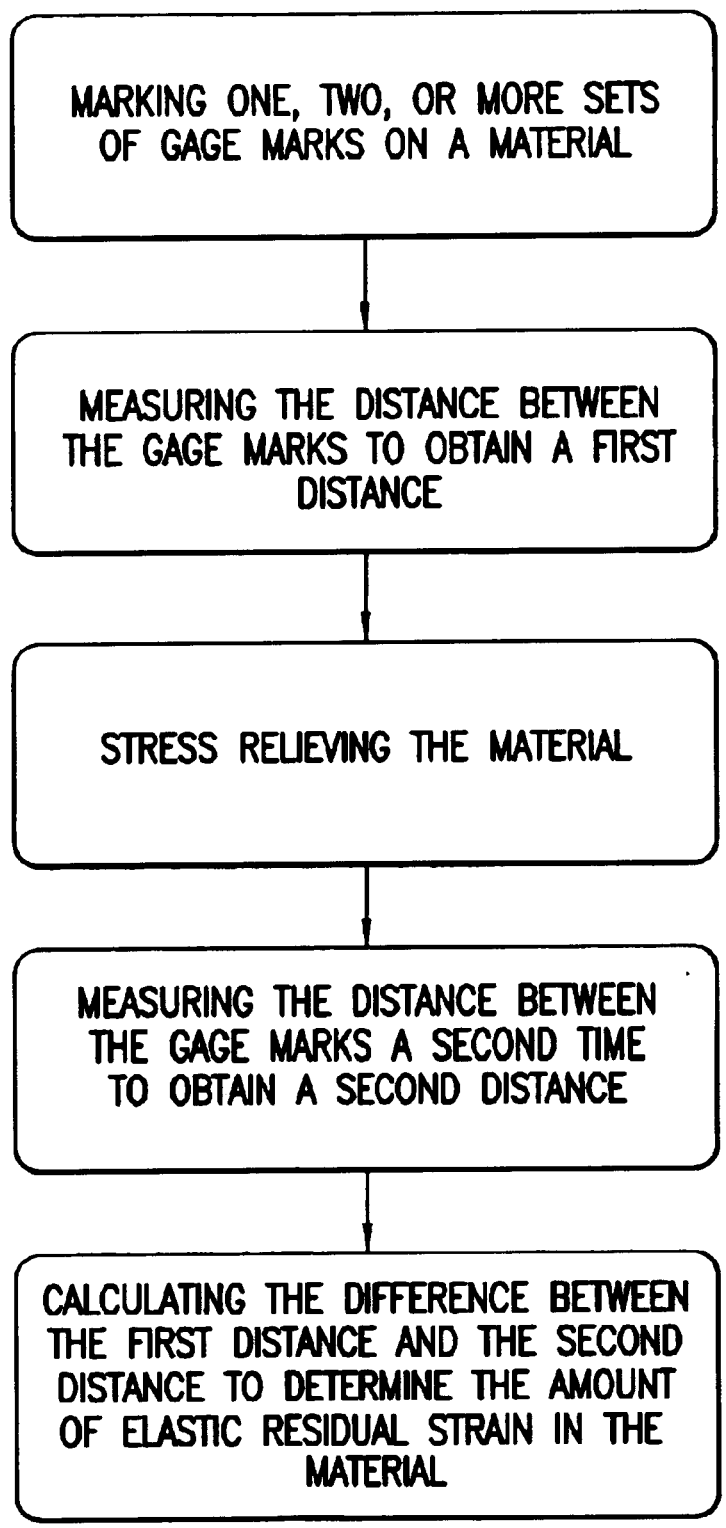
FIG. 3 is a diagram of the concept of the present invention.

The present invention looks at the residual stresses on a macroscopic level, and offers a low cost alternative that can be employed in most machine shops equipped with a toolmakers microscope and a small oven to stress relieve components/test pieces.

It is known that if a machined, mechanically or thermally processed surface is micro-hardness tested it will give a measurement of hardness when compared to its original hardness. When the processing takes place there is some hardening or softening of the surface, depending on the component material and the processing parameters employed. If the component is then carefully stress relieved then the micro-hardness indentations in the machined, mechanically or thermally processed surface could possibly contract or expand depending whether the inherent residual stress of the machined, mechanically or thermally processed surface was tensile or compressive.

Machined, mechanically or thermally processed surfaces could also be micro-hardness tested with micro-hardness indentations being made at right angles to each other to investigate effects due to anisotropy and/or unequal residual stresses. The micro-hardness measurements would be taken on any micro-hardness-testing machine. The specimens would then be stress relieved under controlled conditions. The micro-hardness indentations would then be re-measured by the micro-hardness-testing machine. The results that would be anticipated are that the micro-hardness indentations will expand if the residual stress in the machined, mechanically or thermally processed surface is compressive, or if the residual stress is in tension then the indentations will contract. This amount of expansion and contraction will enable the amount of elastic strain that the processed surface had experienced to be calculated. From this strain measurement and the use of Young's Modulus and Poission's Ratio the amount of residual stress in the processed surface can be calculated.

The present invention marks the machined, mechanically or thermally processed surface with two or more sets of gage marks comprising micro-hardness indentations, or lines made using a vernier height gage or other marks placed on the material, said marks suitable for determining distance between two or more points. If the component is then carefully stress relieved then the distance between the gage marks in the processed surface will either contract or expand depending whether the inherent residual stress of processed surface was tensile or compressive.

The gage marks can be spaced according to the properties of the material being measured and the measuring instrument. The material properties include the type of material and the expected magnitude of the residual stress on the material. The accuracy of the measuring device is also a consideration as the change in the distance between the gage marks after the material is stress relieved must be determined with differences as small as 0.001 inch, or less, with acceptable precision.

Through calculation it has been determined that the gauge marks would have to be 2" apart to allow for measurement on generally available laboratory equipment. These calculations follow. A typical Al-4.5% Cu wrought alloy has the following properties:

| | |
|---|---|
| Tensile Strength ($\sigma TS$) | 60,000 psi |
| 0.2% Yield Strength ($\sigma y$) | 45,000 psi |
| Elongation | 20% |

The Young's modulus of such a material is approximately 10,000,000 or $10^7$ psi. If it is assumed that a unidirectional residual elastic stresses in a component vary between 10% and 100% of the yield stress—a quite likely variation in the case of a cast aluminum version of the alloy [Ansell, 1999], the sensitivity of the method can be estimated in the following manner:

10%σy (Worst Case)

$$\text{Elastic Stress} = 0.1 \times (45 \times 10^3) = 45 \times 10^2 \text{ psi}$$

$$\text{Elastic Strain} = 45 \times 10^2 / \text{Young's Modulus}$$
$$= 45 \times 10^2 / 10^7$$
$$= 4.5 \times 10^{-4}$$

For markings spaced 2" apart the displacement would be given by:

$$\text{Displacement} = \text{Distance between marks} \times \text{Strain}$$
$$= 2 \times (4.5 \times 10^{-4})$$
$$= 9 \times 10^{-4}$$
$$\approx 0.001"$$

Thus, the worst case scenario does not present a problem since instrumentation such as a traveling microscope will be able to measure to 0.001" quite easily.

This scenario does not present a problem with instrumentation as a traveling microscope will be able to measure to 0.001" quite easily. However, other spacing for the gage marks could be used taking into account the material properties and accuracy of the instrument being used for the measurement.

Machined, mechanically or thermally processed surfaces are marked using a vernier height gage, a micro-hardness-testing machine, or any other means apparent to one skilled in the art. The marks are considered gage marks. Block gages or any other means apparent to one skilled in the art can be used to give a reproducible gage length of the appropriate magnitude. Preferably, the gage marks will be made parallel to each other. Additional gage marks can be made at different orientations to each other to eliminate any possibility of errors due to inherent residual stresses in the test piece. The distance between the gage lines are then measured using a traveling microscope or any other means of measuring. Preferably, the gage lines are measured with the aid of gage blocks to allow for quick and accurate movement of the test piece through the gage length. The specimens are then stress relieved under controlled conditions appropriate for that material. The new distance between the gage marks is then re-measured by the traveling microscope or any other means of measuring. Preferably, the gage blocks are used to increase the accuracy and speed of the measurement. This second measurement determines the amount of strain and whether the strain in the machined, mechanically or thermally processed test piece surface is tensile or compressive. Through the use of Young's Modulus, Poission's Ratio and from the measured strains the amount of residual stress that was induced by the processing operation is derived.

Machined, mechanically or thermally processed surfaces are marked using electromechanical devices, mechanical devices, electrical devices, chemical devices, and combinations thereof. Other means for marking the surfaces include human, electrical, steam, and hydraulic powered devices.

The distance between the gage marks can be measured with a vision system although any system of providing accurate measurement will suffice. The preferred vision system detects the relative position of the gage marks or lines and then can transmit the first and second measurement to a computer system for processing. The vision system preferably comprises sensors that detect the gage marks or lines. The sensors employed in the present invention can be infrared, optical, acoustic or any other sensor means that would be apparent to one skilled in the art.

A computer system is used to calculate the amount of elastic residual strain including determining whether the strain is tensile or compressive by using the relative position of the first and second gage marks or lines detected by the vision system. The computer system determines the amount of elastic residual strain and through the use of Young's Modulus, Poission's Ratio and from the measured strain the amount of residual stress that was induced by the processing operation is derived.

Should the material under investigation have previously undergone an aging reaction (e.g. an aluminum alloy in the T6 condition) stress relief is accomplished by overaging. Although the flow stress and thus hardness will change, the elastic modulus does not change significantly, since it depends upon the interatomic forces and not upon the forces required to initiate slip. Thus the present invention can be used to measure the residual stress in such a material.

This invention can be used on various types of metals including but not limited to constructional and tool steels, stainless steels, titanium, aluminum, copper, nickel and zinc based alloys. It would also be applicable to other nonferrous metals and any machinable metals, castable metals, weldable metals, or combinations thereof.

The present invention provides an inexpensive method for determining superficial residual stresses that are present after machining or surface treating a material.

Measurement of these residual stresses at a micro level is a complex process that necessitates the use of sophisticated x-ray, neutron or electron diffraction equipment, requiring highly skilled operators [Callister Jr., 2000; Proffen et al., 1998;Tissue, 2000]. Research has however, been undertaken to determine the effect of residual stresses on micro-hardness indentation size [Simes et al., 1984], which shows promise. Preliminary work utilized pre-stressed cruciform test pieces that were micro-hardness tested [Simes et al., 1984].

It has been demonstrated that the indentation produced by the micro-hardness tester deformed once the tension on the cruciform component was released, thus indicating that micro-hardness testing can determine if a residual stress was either tensile or compressive [Simes et al., 1984]. The use of micro-hardness indentations requires extensive modification of the sample stage of the microscope involved to permit residual stress to be measured in both the longitudinal and latitudinal directions, as the diamond indentation is very small and will give the measurement a low sensitivity.

As an alternative to the above approach, the inventors have provided a more simplistic, economical method. In this method, a previously machined surface is provided with parallel gage marks separated by a given distance. The sample material is then stress-relieved and the change in distance between the gage marks is measured. If the surface had been in tension the distance will have decreased, while had it been in compression it would have increased. This method provides an inexpensive method for determining whether, for example, the surface had been abusively machined. The change in distance between the gage marks would, of course, depend on the material and the machining parameters involved, in particular the cutting speed [Wyatt, 2002].

This method can be easily demonstrated on materials subjected to an abusive machining regime. A specially designed large diameter dual plane balanced face mill can generate cutting speeds up to 3,000 m min-1 (9,000 sfm) on a conventional CNC machining center [Wyatt, 2002; Smith et al., 1998]. The special nature of this face mill provides a cutting regime that has both high impact loads and cutting temperatures applied to the test piece, which are good initiators of residual stresses. Such a mill can be used to machine the materials as it can be readily adapted to work on different materials simply by changing the cutting inserts.

Therefore, through the use of machining equipment and cutters and existing simple instrumentation, which are readily available, abusive machining practices can be identified, which through ratification via x-ray or neutron diffraction techniques can subsequently be developed into the economically viable residual stress analysis technique of the present invention. This technique not only represents an economical approach but can provide a badly needed commercial standard for machine shops. Thus the present invention can benefit many companies, especially in the aerospace and automotive industries.

Exemplary test using the method of the present invention can be conducted on pure aluminum and/or copper, as these materials are easily stress relieved. Should the material under investigation have previously undergone an aging reaction (i.e. as with an aluminum alloy of the 2XXX or 6XXX series) it should be noted that stress relief will be accompanied by averaging. Although the flow stress and thus hardness will change, the elastic moduli will not, since they are dependent upon the interatomic forces rather than the forces required to initiate slip. The machining trials can be undertaken at various cutting speeds and feeds which will be determined through the use of Taguchi techniques, which are well known to those skilled in the art.

The machined surfaces can then be marked using a diamond tipped scriber, a vernier height gauge and slip gauges to provide an accurate gauge length, with pairs of marks being made at right angles to each other to examine transverse as well as longitudinal effects in the as-received billet. The distance between gauge lines can then be measured on a traveling microscope. The specimens can then be stress relieved under controlled conditions. Subsequently the distances between the marks can again be measured by the traveling microscope. This second measurement determines the amount of strain and hence whether the stress in the machined testpiece surface was either tensile or compressive.

It is within the concept of the present invention to provide a model or stress profile for specific materials, which have undergone specific machining processes. Such a profile can be derived by conducting the method of the present invention on a plurality of samples of specific materials that have been machined in a specific manner and from the results obtained, calculate a median or expected result for a wide variety of materials and machining processes. By establishing a baseline or expected result for certain specific criteria in the use of the present invention method, a user can benefit from the expectation that similar results will occur when those specific criteria are met.

The inventors have discovered that the distance between the residual stress gauge marks will expand if the residual stress in the machined surface is compressive, or if the residual stress is in tension then the distance between the gauge marks will contract. The amount of expansion and contraction is readily measurable and using that measurement enables the amount of strain that the machined surface endured to be calculated. The present invention greatly enhance the determination of residual stress, and will be a helpful tool for many researchers in the field of machining who do not have access to expensive x-ray or electron diffraction equipment. Also, as indicated above, a method of establishing a new standard for the estimation of residual stresses in the macro environment has been developed.

The present invention also provides an alternative method for determining residual stress in abusively machined surfaces. This alternative method provides an inexpensive process for determining residual stress levels and whether they are tensile or compressive in nature; and underlines the need to appreciate the impact of abusive machining practices.

Measurement of residual stresses is a complex process that requires the use of sophisticated x-ray diffraction equipment, requiring highly skilled operators [Callister Jr., 2000]. Work has been undertaken to utilize micro-hardness testing to determine the levels of residual stress [Askeland, 1990]. However, the problem with micro-hardness testing is that although it gives a level of residual stress it does not indicate whether that stress is tensile or compressive. If micro-hardness testing could tell this important aspect of residual stress characteristics it would be beneficial in making micro-hardness testing an inexpensive alternative to x-ray diffraction techniques. Work has been undertaken utilizing pre-stressed cruciform testpieces that were micro-hardness tested [Simes et al., 1984]. This work demonstrated the indentation produced by the micro-hardness testing machine did deform once the tension on the cruciform component was released, thus showing that micro-hardness testing could determine if a residual stress was either tensile or compressive.

If a machined surface is micro-hardness tested it will give a different measurement of the hardness of the machined surface when compared to its original hardness. If abusive machining takes place there will be some hardening or softening of the machined surface, depending on the component material and the machining parameters employed, especially cutting speed [Wyatt, 2002]. If the component was then carefully stress relieved then the micro-hardness indentations in the machined surface will either contract or expand depending whether the inherent residual stress of the machined surface was tensile or compressive. To undertake such a study an abusive machining regime must be performed on the testpieces.

The inventors have thus discovered that through the use of machining equipment and cutters that are available at little cost, and a modestly equipped metallurgy laboratory, abusive machining practices can be identified, which through ratification via x-ray diffraction techniques can be developed into an economically viable residual stress analysis technique. This cost-effective technique can provide a commercial standard for machine shops. Another benefit would be that such techniques would also provide a completely documented machined surface characterization service. A service such as this can be invaluable to companies in need of an economical and highly accurate predictive method for evaluating new machining practices. The savings to such industries as the automotive or aviation industries would be enormous.

In developing this alternative method, the initial tests will be undertaken on pure aluminum and/or copper, as these materials are easily stress relieved. The machining trials are undertaken at various cutting speeds and feeds which will be determined through the use of Taguchi techniques, as before.

The machined surfaces can then be micro-hardness tested with the indentations being made at right angles to each other to eliminate any possibility of errors. The micro-hardness measurements can be taken on the micro-hardness-testing machine and as a check they can be re-measured on a scanning electron microscope (SEM). The specimens can then be stress relieved under controlled conditions. The micro-hardness indentations can then be measured by both the micro-hardness-testing machine and the SEM. This second measurement determines if the stress in the machined testpiece surface was either tensile or compressive.

A number of tests using the method of the present invention can be undertaken at each of the selected machining parameters and a full statistical analysis of the results can then be undertaken to give a degree of confidence to the final conclusions and expected results in developing a model or stress profile.

Employing this alternative method, the micro-hardness indentations will expand if the residual stress in the machined surface is compressive, or if the residual stress is in tension then the indentations will contract. This amount of expansion and contraction will enable the amount of strain that the machine surface had endured to be calculated. This method greatly enhances the use of micro-hardness testing as a tool for the determination of residual stress, and can help many researchers in the field of machining who do not have access to expensive x-ray diffraction equipment.

All references cited with this application and listed below are herein fully incorporated by reference. Variations, modifications, and additions to this invention will be readily apparent to one skilled in the art and such modifications and additions would be fully within the scope of the invention, which is limited only by the following claims.

REFERENCES

1. MERCHANT M. E., 1999, Evolution of the Modeling of Machining in the 20th Century—an Interpretive Look at American Contributors, Third International Conference on Industrial Tooling, September 7th & 8th, pp. 1–7
2. DEWES R. C., ASPINWALL D. K., WISE M. L. H., 1995, High Speed Machining—Cutting Tools and Machine Requirements, Proceedings of the 31 st International Matador Conference, April, pp. 455–461
3. WYATT J. E. 2002, High Speed Face and End Milling of Stainless Steel Grades, Ph.D. Thesis, Southampton Institute, UK.
4. DEWES R. C. ASPINWALL D. K., 1996, The use of High Speed Machining for the Manufacture of Hardened Steel Dies, Transactions of the North American Manufacturing Research Institution of SME, Vol. XXIV, May 21–23, pp. 21–26
5. SMITH G. T., WYATT J. E. & HOPE A. D., 1998, Ultra-High Speed Face Milling of Stainless Steels Utilising Large Dual-Plane Balanced Cutters, Presented at Behaviour of Materials in Machining —Opportunities and Prospects for Improved Operations, 12–13 November, pp. 199–207
6. LIU C R, LIN Z C, BARASH M N, 1984, Thermal and Mechanical Stresses in the Workpiece During Machining, High Speed Machining, Presented at the Winter Annual Meeting of the ASME, December 9–14, USA
7. ARNDT G, 1971, On The Study of Metal Cutting and Deformation at Ultra-High-Speeds, Proceedings of the Conference of Production Science Industry, Monash University, Vol. 30, pp. 30–41
8. SCHULTZ H., 1984, High-Speed Milling of Aluminium Alloys, High Speed Machining, Presented at the Winter Annual Meeting of the ASME, December 9–14, USA
9. KALPAKJIAN S., SCHMID S. R. 2001, Manufacturing Engineering and Technology—Third Edition, Addison—Wesley Publishing Company (U.S.A.), ISBN 0-201-36131-0
10. HENRICKSEN E. K., 1951, Residual Stresses in Machined Surfaces, Transactions of ASME, Vol 73, page 69
11. LIU C. R., GUO Y. B., 2000, Finite Element Analysis of the Effect of Sequential Cuts and Tool-Chip Friction on Residual Stresses in a Machined Layer, International Journal of Mechanical Sciences, Vol 42 (6), pp. 1069–1086
12. GUO Y. B., Liu C. R., 2000, Residual Stress Formation Mechanism and its Control by Sequential Cuts, Transactions of NAMRI/SME, Vol 28, pp. 179–183
13. HEYMES F., COMMET B., Du BOST B., LASSINCE P., LEQUEU P., RAYNAUD G.-M., 1997, Development of New Aluminium Alloys for Distortion Free Machined Aluminium Aircraft Components, Proceedings of the 1 st ASM International Non-Ferrous Processing and Technology Conference, 10–12 Mar., St. Louis, Mo., U.S.
14. ANSELL H., 1999, Fatigue and Damage Tolerance Aspects of High Speed Machined Airframe Parts, Meeting of the International Committee on Aeronautical Fatigue, July, Bellevue, Wash.
15. BLOM A. F., PALMBERG B., 2001, A Review of Aeronautical Fatigue Investigations in Sweden During the Period June 1999 to May 2001, Swedish Defence Research Agency, FOI, The Aeronautics Division, FFA, Sweden, FOI-R-0138-SE
16. FITZSIMMONS M., EL WARDANY T., FITZPATRICK P., 2000, Efficient Machining of Titanium Rotorcraft Components, Helicopter Society, 56th Forum, May
17. MARCHAL, Y., 2003, Private correspondence between Dr. Marchal of Sonaca SA and Dr J T Berry & Dr. J E Wyatt of Mississippi State University
18. PEYRONEL, S, 2002, Private correspondence between Dr. Peyronel of Aermacchi and Dr J T Berry of Mississippi State University
19. CALLISTER Jr. W. D., 2000, Materials Science and Engineering an Introduction, Fifth Edition, John Wiley & Sons, New York, ISBN 0-471-32013-7
20. PROFFEN T. H., NEDER R. R., 1998, Teaching Guide X-Ray & Neutron Diffraction, http://www.kri.physik.uni-muenchen.de/geo/crystal/teaching/teaching.html
21. TISSUE B. M., 2000, Chemistry Hypermedia Project, http://www.chem.vt.edu/chem-ed/diffraction/neutron.html
22. SIMES T. R., MELLOR S. G., HILLS D. A., 1984, A Note on the Influence of Residual Stress on Measured Hardness, Research Note, Journal of Strain Analysis Vol19 (2), pp. 135–137
23. CAMPBELL J., 2001, Private communication between Professor Campbell and J. T. Berry
24. ASKELAND D. R., 1990, The Science and Engineering of Materials, Second Edition, Chapman Hall, London, ISBN 0-412-34260-X

What is claimed is:
1. A method of determining the residual stress of a material, the method comprising:
marking the material with at least two sets of gage marks, said sets of gage marks each comprising a first mark and a second mark, measuring a first distance between said first mark and said second mark of each of said sets of gage marks, stress relieving the material, measuring a second distance between said first mark and said second mark of each of sets of gage marks, and calculating the difference between the first distance and the second distance, and thereby determining the amount of elastic residual strain in the material.

2. The method of claim 1, wherein the marking is done by a device, which is selected from the group consisting of an electromechanical device, a mechanical device, an electrical device, a chemical device, or combinations thereof.

3. The method of claim 1, wherein the marking is done by a micro-hardness-testing machine.

4. The method of claim 1, wherein the marking is done by a device powered by human, electrical, steam, or hydraulic power.

5. The method of claim 1, wherein the measuring of the first distance and the measuring of the second distance is done by a vision system that can detect the relative position of the one or more sets of gage marks.

6. The method of claim 1, wherein the measuring of the first distance and the measuring of the second distance is done by a system employing at least one sensor capable of recognizing said gage marks, said sensor being selected from the group consisting of mechanical, infrared, optical, acoustic, or combinations thereof.

7. The method of claim 1, wherein the marking of material is done such that said sets of gage marks are in different orientations from each other.

8. The method of claim 1, wherein the marking of material is done such that said sets of gage marks are lines which are parallel to each other.

9. The method of claim 1, wherein the marking of material is done such that said sets of gage marks are made at right angles to each other.

10. The method of claim 1, wherein the calculating step for determining the amount of elastic residual strain is accomplished with the aid of a computer system.

11. The method of claim 10, wherein the computer system further aids in the determination of whether the strain is tensile or compressive by using the relative position of the first and second sets of gage marks.

12. The method of claim 10, the computer system uses Young's Modulus, Poisson's Ratio, and the measured strains the amount of residual stress that was induced by the machining operation is thus derived.

13. The method of claim 1, wherein the surface of said material has undergone machining, mechanical, or thermal processing.

14. The method of claim 1, wherein said measuring at least one of said first distance and said second distance comprises using a traveling microscope.

15. The method of claim 1, wherein the marking is done using a vernier height gage is used to mark the material.

16. The method of claim 1, wherein marking the material comprises using block gages to give an accurate gage length.

17. The method of claim 16, wherein the block gages are used for measuring the first distance to allow for quick and accurate movement of the test piece through the gage length.

18. The method of claim 16, wherein the block gages are used for measuring the second distance to allow for quick and accurate movement of the test piece through the gage length.

19. The method of claim 1, wherein the calculating includes the use of Young's Modulus, Poisson's Ratio, and the measured strains the amount of residual stress that was induced by the machining operation is thus derived.

20. The method of claim 1, wherein the material is selected from the group consisting of constructional and tool steels, stainless steels, titanium, aluminum, copper, nickel and zinc based alloys, nonferrous metals, machinable metals, castable metals, weldable metals, or combinations thereof.

21. A method of determining the residual stress of a material, the method comprising:

marking the material with at least one set of gage marks, said at least one set of cage marks comprising a first mark and a second mark for each of said at least one set of gage marks, measuring a first distance between said first mark and said second mark of each of said at least one set of gage marks, stress relieving the material, measuring a second distance between said first mark and said second mark of each of said at least one set of gage marks, and calculating the difference between the first distance and the second distance, and thereby determining the amount of elastic residual strain in the material.

22. A system that can be used to determine the residual stress of a material, the system comprising:

a marking device for marking the material with at least one set of gage marks, each of said at least one set of gate marks comprising a first mark and a second mark, a measuring device for measuring a first distance between said first mark and said second mark of each of said at least one set of gage marks, a device for stress releasing the material, a second measuring device for measuring a second distance between said first mark and said second mark of each of said at least one set of gage marks, a calculating device for calculating the difference between the first distance and the second distance, and thereby determining the amount of elastic residual strain in the material.

23. The system of claim 22, wherein the marking device is selected from the group consisting of an electromechanical device, a mechanical device, an electrical device, a chemical device, or combinations thereof.

24. The system of claim 22, wherein the marking device is a micro-hardness-testing machine.

25. The system of claim 22, wherein the marking device is powered by human, electrical, steam, or hydraulic power.

26. The system of claim 22, wherein the measuring device is a vision system that can detect the relative position of the one or more sets of gage marks.

27. The system of claim 22, wherein the measuring device is a system employing at least one sensor capable of recognizing said gage marks, said sensor being selected from the group consisting of mechanical, infrared, optical, acoustic, or combinations thereof.

28. The system of claim 22, wherein the marking device is capable of making the gage marks in different orientations from each other.

29. The system of claim 22, wherein the marking device is capable of marking the gage marks as lines which are parallel to each other.

30. The system of claim 22, wherein the marking device is capable of marking the gage marks at right angles to each other.

31. The system of claim 22, wherein the calculating device comprises a computer system.

32. The system of claim 31, wherein the computer system is capable of also determining whether the strain is tensile or compressive by using the relative position of the first and second gage marks.

33. The system of claim 31, wherein the computer system is capable of using Young's Modulus, Poisson's Ratio, and the measured strains the amount of residual stress that was induced by the machining operation is thus derived.

34. The system of claim 22, wherein the surface of said material has undergone machining, mechanical, or thermal processing.

35. The system of claim 22, wherein said measuring device used for measuring the first distance, the second distance, or both comprises a traveling microscope.

36. The system of claim 22, wherein the marking device is a vernier height gage.

37. The system of claim 22, wherein the marking device comprises block gages to give an accurate gage length.

38. The system of claim 37, wherein the block gages are used for measuring the first distance to allow for quick and accurate movement of the test piece through the gage length.

39. The system of claim 37, wherein the block gages are used for measuring the second distance to allow for quick and accurate movement of the test piece through the gage length.

40. The system of claim 22, wherein the calculating device comprises the use of Young's Modulus, Poisson's Rule, and the measured strains the amount of residual stress that was induced by the machining operation is thus derived.

41. The system of claim 22, wherein the material is selected from the group consisting of constructional and tool steels, stainless steels, titanium, aluminum, copper, nickel and zinc based alloys, nonferrous metals, machinable metals, castable metals, weldable metals, or combinations thereof.

42. A system that can be used to determine the residual stress of a material, the system comprising:
 a means for marking the material with one or more sets of gage marks or lines, said one or more sets of gage marks or lines comprising a first mark or line and a second mark or line for each of said one or more sets of sage marks or lines,
 a means for measuring the first distance between said first mark or line and said second mark or line of each of said one or more sets of gage marks or lines,
 a means for stress relieving the material,
 a means for measuring a second distance between said first mark or line and said second mark or line of each of said one or more sets of gage marks or lines, and
 a means for calculating the difference between the first distance and the second distance, and thereby determining the amount of elastic residual strain in the material.

43. The system of claim 42, wherein the means for marking is selected from the group consisting of an electromechanical device, a mechanical device, an electrical device, a chemical device, or combinations thereof.

44. The system of claim 42, wherein the means for marking is a micro-hardness-testing machine.

45. The system of claim 42, wherein the means for marking is powered by human, electrical, steam, or hydraulic power.

46. The system of claim 42, wherein the means for measuring is a vision system that can detect the relative position of the one or more sets of gage marks.

47. The system of claim 42, wherein the means for measuring is a system employing at least one sensor capable of recognizing said gage marks, said sensor being selected from the group consisting of mechanical, infrared, optical, acoustic, or combinations thereof.

48. The system of claim 42, wherein the means for marking is capable of making the gage marks in different orientations from each other.

49. The system of claim 42, wherein the means for marking is capable of marking the gage marks as lines which are parallel to each other.

50. The system of claim 42, wherein the means for marking is capable of marking the gage marks at right angles to each other.

51. The system of claim 42, wherein the means for calculating comprises a computer system.

52. The system of claim 51, wherein the computer system is capable of also determining whether the strain is tensile or compressive by using the relative position of the first and second gage marks.

53. The system of claim 51, wherein the computer system is capable of using Young's Modulus, Poisson's Rule, and the measured strains the amount of residual stress that was induced by the machining operation is thus derived.

54. The system of claim 42, wherein the surface of said material has undergone machining, mechanical, or thermal processing.

55. The system of claim 42, wherein the means for measuring used for measuring the first distance, the second distance, or both comprises a traveling microscope.

56. The system of claim 42, wherein the means for marking is a vernier height gage.

57. The system of claim 42, wherein the means for marking comprises block gages to give an accurate gage length.

58. The system of claim 57, wherein the block gages are used for measuring the first distance to allow for quick and accurate movement of the test piece through the gage length.

59. The system of claim 57, wherein the block gages are used for measuring the second distance to allow for quick and accurate movement of the test piece through the gage length.

60. The system of claim 42, wherein the means for calculating comprises the use of Young's Modulus, Poisson's Rule, and the measured strains the amount of residual stress that was induced by the machining operation is thus derived.

61. The system of claim 42, wherein the material is selected from the group consisting of constructional and tool steels, stainless steels, titanium, aluminum, copper, nickel and zinc based alloys, nonferrous metals, machinable metals, castable metals, weldable metals, or combinations thereof.

62. A method of determining the residual stress of a material and whether the residual stress is tensile or compressive in nature, the method comprising:
 marking the material with a first gage mark and a second gate mark,
 measuring a first distance between said first gage mark and said second gage mark,
 stress relieving the material,
 measuring a second distance between said first gage mark and said second gage mark, and
 calculating the difference between the first distance and the second distance, and thereby determining the amount of elastic residual strain in the material and whether the residual strain is tensile or compressive in nature.

63. A method of modeling of a component residual stress from production of raw billet through to finished machined component, the method comprising:

determining the residual stress of a material a first time, according to the method of claim 1 and making a record of the amount of elastic residual strain in the said material, repeating the method of claim 1 on other materials of identical nature and machine treatment history as the material of said first time and making a record of the amount of elastic residual strain for the other material for each repeated method of claim 1, so as to compile a library of results for said repeated methods of claim 1, and analyzing said library of results, whereby said analysis provides an expected outcome or profile of elastic residual strain for materials identical in nature and machine treatment history, repeating the above process so as to compile a data base of different materials and different machine histories of those materials such that said expected outcome can be used as a predictive model for determining the residual stress of a material from raw billet through to finished machined component.

* * * * *